United States Patent

Uusivirta et al.

(10) Patent No.: US 10,429,285 B2
(45) Date of Patent: Oct. 1, 2019

(54) APPARATUS FOR CHECKING NEED FOR MAINTENANCE AND VISCOMETER

(71) Applicant: VALMET AUTOMATION OY, Espoo (FI)

(72) Inventors: Lauri Uusivirta, Lempäälä (FI); Matti T. Mäkelä, Haukipudas (FI)

(73) Assignee: VALMET AUTOMATION OY, Espoo (FI)

( * ) Notice: Subject to any disclaimer, the term of this patent is extended or adjusted under 35 U.S.C. 154(b) by 178 days.

(21) Appl. No.: 15/452,141

(22) Filed: Mar. 7, 2017

(65) Prior Publication Data

US 2017/0268975 A1 Sep. 21, 2017

(30) Foreign Application Priority Data

Mar. 17, 2016 (FI) ...................................... 20165221

(51) Int. Cl.
| | |
|---|---|
| *G01N 11/14* | (2006.01) |
| *G01N 11/00* | (2006.01) |
| *G01N 11/10* | (2006.01) |

(52) U.S. Cl.
CPC .............. *G01N 11/14* (2013.01); *G01N 11/00* (2013.01); *G01N 11/10* (2013.01); *G01N 11/105* (2013.01); *G01N 2011/0006* (2013.01)

(58) Field of Classification Search
CPC ...... G01N 11/14; G01N 11/00; G01N 11/105; G01N 11/10; G01N 2011/0006
USPC ....................................................... 73/54.01
See application file for complete search history.

(56) References Cited

U.S. PATENT DOCUMENTS

| | | | |
|---|---|---|---|
| 3,364,730 A | 1/1968 | Wall | |
| 3,796,088 A | 3/1974 | Gustafsson et al. | |
| 4,062,226 A | 12/1977 | Hietala | |
| 4,148,215 A * | 4/1979 | Hofstetter, Jr. ........ | G01N 11/14 73/54.23 |
| 4,595,487 A | 6/1986 | Nunlist | |
| 4,757,708 A | 7/1988 | Hietaranta | |
| 5,531,102 A | 7/1996 | Brookfield et al. | |
| 5,600,058 A * | 2/1997 | Preikschat ............. | G01N 11/14 73/54.32 |
| 5,686,660 A * | 11/1997 | Lundberg ............... | G01N 11/14 73/53.03 |
| 5,844,152 A * | 12/1998 | Lambert ................. | G01N 11/10 73/866.5 |

(Continued)

FOREIGN PATENT DOCUMENTS

WO 2008/132282 A1 11/2008

OTHER PUBLICATIONS

Aug. 21, 2017 Search Report issued in European Patent Application No. 17 16 0987.

(Continued)

*Primary Examiner* — Marrit Eyassu
(74) *Attorney, Agent, or Firm* — Oliff PLC

(57) ABSTRACT

An apparatus for checking a need for maintenance of a viscometer measuring consistency of suspension comprises a rigid rod and an elongated cavity in a measuring arm of the viscometer. The rigid rod is matched with the cavity for the rod to be movable in the cavity. The cavity is configured to become mismatched with respect to the rod in response to a bending of the measuring arm, the mismatch indicating a need for maintenance of the viscometer.

11 Claims, 3 Drawing Sheets

(56) References Cited

U.S. PATENT DOCUMENTS

| | | | |
|---|---|---|---|
| 6,324,921 B1 | 12/2001 | Hietaranta et al. | |
| 2007/0193344 A1* | 8/2007 | Haapasaari | G01N 11/14 73/61.41 |
| 2010/0154520 A1* | 6/2010 | Schubert | G01N 11/14 73/54.28 |
| 2011/0162440 A1 | 7/2011 | Lundberg et al. | |

OTHER PUBLICATIONS

May 10, 2016 Search Report issued in Finnish Patent Application No. 20165221.

* cited by examiner

APPARATUS FOR CHECKING NEED FOR MAINTENANCE AND VISCOMETER

FIELD

The invention relates to an apparatus for checking need for maintenance of a viscometer and a viscometer.

BACKGROUND

The cone spindle of a blade transmitter, which measures consistency of pulp slurry, is typically designed to bend in an over load condition. The purpose of the bending is to protect bearings and other internal parts of the blade transmitter. On the other hand, the bending has a negative effect on accuracy of the consistency measurements. Furthermore, it is impossible to know whether the cone spindle has bent or not without detaching the blade transmitter from the process pipe and performing a visual checking. The checking is undesirable because it requires a stoppage of the process operation. A similar problem exists also when other kind of viscometers such as a rotating consistency meter are used. Hence, there is a need to improve the checking.

BRIEF DESCRIPTION

The present invention seeks to provide an improvement. According to an aspect of the present invention, there is provided an apparatus for checking a need for maintenance of a viscometer measuring consistency of suspension, the apparatus comprising a rigid rod and an elongated cavity inside a measuring arm of the viscometer; the rigid rod is matched with the cavity for the rod to be movable in the cavity; and the cavity is configured to become mismatched with respect to the rod in response to a bending of the measuring arm, the mismatch indicating a need for maintenance of the viscometer.

According to another aspect of the present invention, there is provided a viscometer for measuring consistency of suspension, the viscometer comprising a rigid rod and a measuring arm, a first end which is coupled with a projection insertable in the suspension; the measuring arm comprises an elongated cavity; the rigid rod is matched with the cavity for the rod to be movable in the cavity; and the cavity is configured to become mismatched with respect to the rod in response to a bending of the measuring arm, the mismatch indicating a need for maintenance of the viscometer.

The invention has advantages. The deformation of a measuring arm such as the cone spindle can be checked without a stoppage of the process operation.

LIST OF DRAWINGS

Example embodiments of the present invention are described below, by way of example only, with reference to the accompanying drawings, in which FIG. 1 illustrates an example an apparatus for checking a need for maintenance of a viscometer measuring consistency of suspension;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, such features have not been discussed in more detail here.

Figure 1:
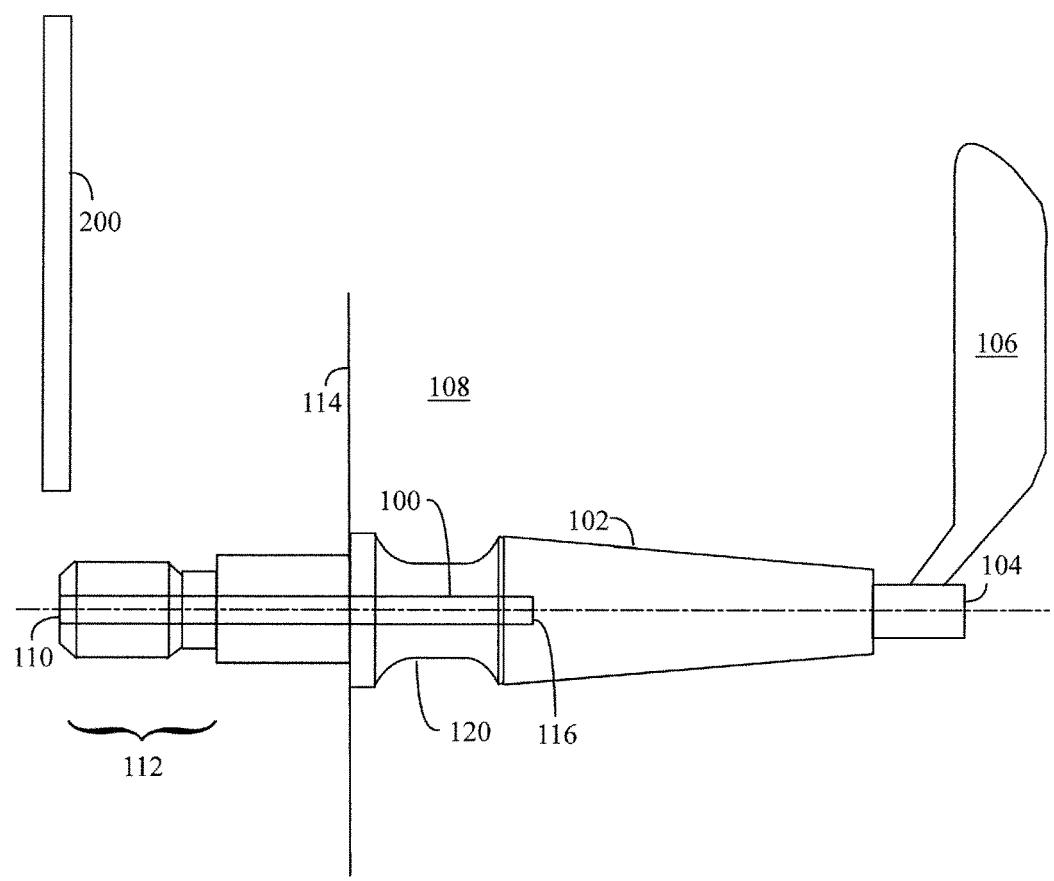
Figure 2:
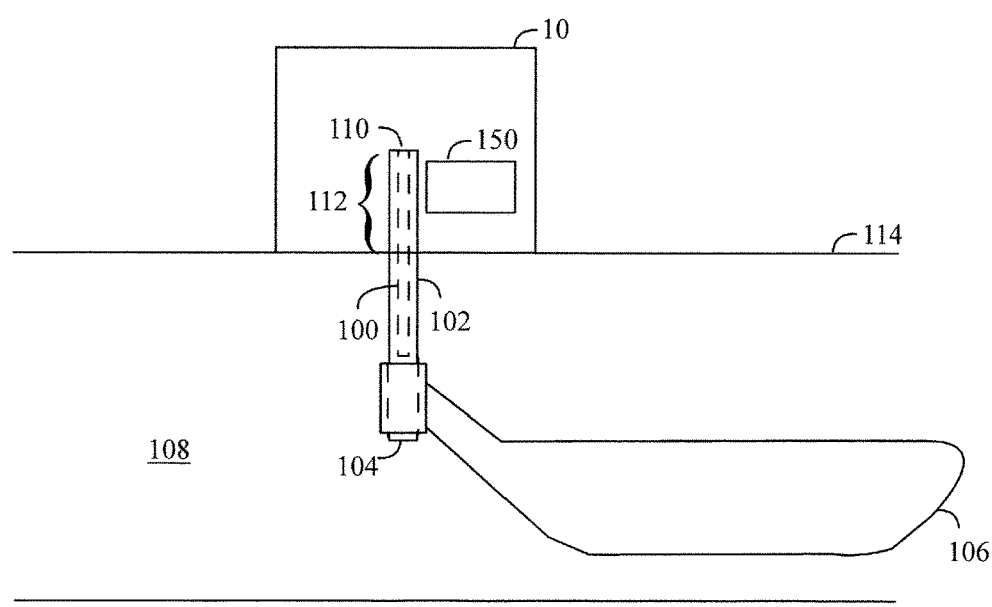
FIG. 2 illustrates an example of a viscometer.

Look at FIGS. 1 and 2 now. FIG. 1 presents an example an apparatus for checking a need for maintenance of a viscometer measuring consistency of suspension. FIG. 2 presents an example of the viscometer 10. The name of viscometer 10 is used for a meter measuring consistency or viscosity. The viscometer 10 may also be called a rheometer if it measures consistency or viscosity. The suspension may be pulp slurry or the like, for example. The apparatus comprises an elongated cavity 100 inside a measuring arm 102 of the viscometer 10 and a rigid rod 200. The measuring arm 102 may be made of metal such as steel, for example. The rigid rod 200 is matched with the cavity 100 for the rod 200 to be movable in the cavity 100. The rod 200 and the cavity 100 are counterparts which fit together. The rod 200 and the cavity 100 may be machined within desirable tolerance requirements in order to be matched together. The tolerance between part diameters may be h7/H7, for example. The cavity 100 has a bottom 116 inside the measuring arm 102. The bottom 116 may be at a location which is inside the process pipe 114 when the viscometer 10 is mounted on the process pipe 114.

In more detail, the measurement arm 102 may comprise a spindle which actually includes the cavity 100. The spindle may be a cone spindle (see FIG. 1) which has a narrowed section 120. The narrowed section 120 has a diameter which is smaller than that of sections directly adjacent to it on both sides. The narrowed section 120 bends easier than other sections and thus concentrates deforms and damages to itself. The spindle is a mechanical part often made of metal.

If the measurement arm 102 has the narrowed section 120, the cavity 100 and the rod 200 in the cavity 100 extends through it to both sides thereof.

The non-deformed rod 200 is movable along the full length of the non-deformed cavity 100. A length of the non-deformed rod 200 may be equal to or longer than a length of the cavity 100.

In an embodiment, the rod 200 may be inserted in the cavity 100 but the rod 200 is not necessarily taken out from the cavity 100 between the checks for the need for maintenance.

The cavity 100 becomes mismatched with respect to the rod 200 in response to a bending of the measuring arm 102. The mismatch may then indicate directly or indirectly the need for maintenance of the viscometer.

In an embodiment, the non-deformed rod 200 may repeatedly be inserted in and removed from the non-deformed cavity 100. The checking of the need for maintenance may be performed by attempting to move the rod 200 in the cavity 100 by insert and removal (or removal and insert) or otherwise back and forth.

The viscometer 10 comprises the apparatus for checking the need for maintenance of the viscometer 10. A first end 104 of the measuring arm 102 of the viscometer 10 is coupled with a projection 106, and the projection 106 is insertable in the suspension 108 flowing or residing in the process pipe 114. The projection 106 of the viscometer 10 causes shear forces to the pulp slurry because the pulp slurry 108 and the projection 106 move with respect to each other. The pulp slurry 108 may flow in the process pipe 114 or the measurement arm 102 may move the projection 106 in the pulp slurry 108.

In an embodiment, the viscometer 10 may be a blade transmitter and the projection 106 thus represents the blade. The blade may be directed parallel to the direction of the flow in the process pipe 114. These forces of the flowing pulp slurry may tilt the projection 106. The tilt, which is related to the consistency of the pulp slurry, may then be measured by a sensor 150. The sensor may be a displacement sensor, a force sensor or the like.

In an embodiment, the viscometer 10 may be a rotating consistency meter which has a drive shaft and a measuring shaft. The measuring shaft, which represented by the measuring arm 102, may be within the drive shaft, and the measuring shaft may have one or more projections 106. The measuring shaft is flexibly mounted with bearings on the drive shaft, which makes an inter-shaft swivel possible. The pulp slurry tries to slow down the rotation of the projections with its consistency which causes a torque between the shafts. The torque, which is related to the consistency of the pulp slurry, may then be measured by a sensor.

Although the rotating consistency meter has structural differences with the blade transmitter, the structure of inserting a projection 106 into suspension which is supported by the measuring arm 102 is similar. Also the problems with the measuring arm 102 are similar.

The mismatch between the cavity 100 and the rod 200 may be caused by a strong impulse from the suspension to the projection 106 or it may be a result of fatigue. The mismatch may represent damage to the usefulness. The measuring arm 102 may bend temporally or permanently because of the strong impulse or fatigue. The mismatch between the cavity 100 and the rod may appear as a loss of at least one degree of freedom or in a difference of shape.

The loss of these features may be detected by a manual or automatic test. In a manual test, a force of bare fingers may be used to insert and/or remove the rod 200. Alternatively, a force of manual tools may be used to insert and/or remove the rod 200. In automatic tests, the forces may be measured by a sensor and compared with a data processing unit. In automatic tests, the forces may also be limited because only weak forces are required for the checking. The maximum force may be limited to 100 N or 5 Nm torque for a threaded rod 200. If the rod 200 can be moved outwards from the cavity 100 or inwards inside the cavity 100 with the same force range as when it was inserted in the non-deformed cavity 100, there is no mismatch and there is no need for maintenance. If the rod 200 cannot be moved outwards from the cavity 100 or inwards inside the cavity 100 with the same force range as when it was inserted in the non-deformed cavity 100, there is a mismatch and there is a need for maintenance.

The loss of the degree of freedom may be tested by attempting to rotate the rod 200 around its longitudinal axis when the rod 200 is in the cavity 100 reaching at least approximately to the bottom 116 of the cavity 100. If the rod 200 can be rotated with the same force range as when it was inserted in the non-deformed cavity 100, there is no mismatch and there is no need for maintenance. If the rod 200 cannot be rotated with the same force range as when it was inserted in the non-deformed cavity 100, there is a mismatch and there is a need for maintenance. This applies to a rod 200 made of flexible material a change of a shape of which is spontaneously irreversible. The flexible material can bend or can be bent without breakage.

The shape of the cavity 100 may deform permanently when the measurement arm 102 is bent. In an embodiment, the rod 200 need not to be in the cavity 100 continuously but the rod 200 may be inserted or attempted be inserted only when making a test to check the need for maintenance of the viscometer 10. If the shape of the cavity 100 has deformed permanently, the rod 200 cannot be inserted into the cavity 100 such that it reaches down to the bottom 116. That the rod 200 cannot be inserted fully in the cavity 100 is an indication of a need for maintenance. If the rod 200 can be inserted in the cavity 100 it is an indication that the measuring arm 102 is in an acceptable condition.

Figure 3:
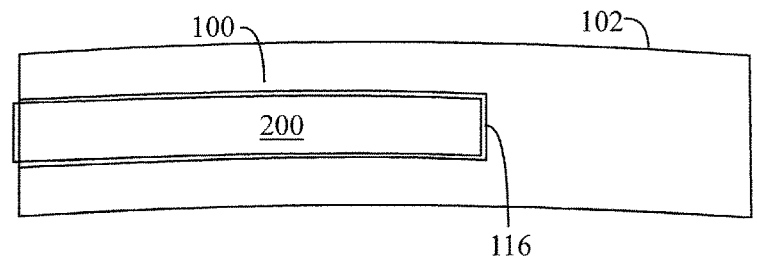
FIG. 3 illustrates an example of a bent measurement arm.

In an embodiment an example of which is illustrated in FIG. 3, the rod 200 may be in the cavity 100 continuously.

In the example of FIG. 3 the measurement arm 102 has bent. The cavity 100 and the rod 100 inside the cavity 100 may also have bent. The rod 200 may be made of a flexible material a change of a shape of which is spontaneously irreversible. The rod 200 may be made of metal such as steel, for example. Because of the deformation the rod 200 may be difficult or impossible to remove from the cavity 100. Particularly, the rod 200 it may be difficult or impossible to rotate the rod 200 in the cavity 100.

If the shape of the cavity 100 has deformed permanently or the shape of the rod 100 has deformed permanently or both shapes have deformed permanently, then the rod 200 cannot be removed fully from the cavity 100 with a force comparable to the inserting force. That the rod 200 cannot be removed fully from the cavity 100 is an indication of a need for maintenance. This applies to a rod 200 made of flexible material a change of a shape of which is spontaneously irreversible.

In an embodiment, the rod 200 may have broken in the cavity 100 which also leads to the situation that the rod 200 cannot be removed fully in one piece from the cavity 100. The broken rod 200 is an indication of a need for maintenance. The breakdown of the rod 200 may be caused by a reversible or irreversible bending of the measurement arm 102. In some cases, a reversible bending of the measuring arm 102 may be a reason to exchange the measuring arm 102 or maintain the measuring arm 102.

In general, at least one of the following may be caused to the rod 200 inside of the cavity 100 in response to the bending of the measuring arm 102 which requires maintenance: the immobilization in the cavity 100, and the breakdown of the rod 200. All in all, at least one of the following may be caused to the rod 200 in response to the bending of the measuring arm 102 which requires maintenance: immobilization in the cavity 100, a loss of the possibility of the insertion into the cavity 100, and a breakdown of the rod 200.

In embodiments examples of which are illustrated in FIGS. 1 and 2, the longitudinal axis of the cavity 100 may be parallel to the longitudinal axis of the measurement arm 102. In an embodiment, the longitudinal axis of the cavity 100 and the longitudinal axis of the measurement arm 102 may be co-axial.

Figure 4:
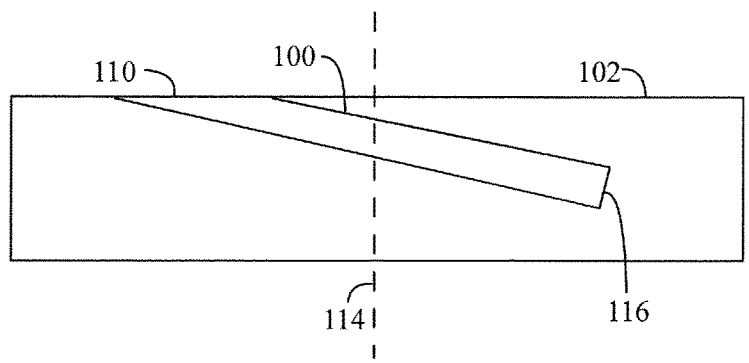
FIG. 4 illustrates an example of a cavity tilted with respect to the longitudinal axis of the measuring arm.

In an embodiment an example of which is illustrated in FIG. 4, the longitudinal axis of the cavity 100 may deviate from a direction parallel to the longitudinal axis of the measurement arm 102 and a direction perpendicular to the longitudinal axis of the measurement arm 102.

Figure 5:
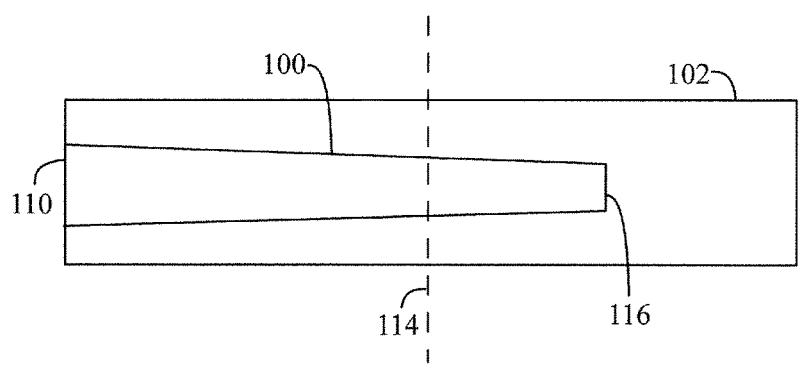
FIG. 5 illustrates an example of a truncated conical cavity.

In an embodiment example of which is shown in FIG. 5, a cross section of the cavity 100, a normal of which is parallel to the longitudinal axis of the cavity 100, is constant or constantly converging towards the first end 104. In an embodiment (a minor variation to example in FIG. 5), a cross section of the cavity 100, a normal of which is in a direction different from a direction perpendicular to the longitudinal axis of the cavity 100, is constant or constantly converging towards the first end 104. A longitudinal axis of the cavity 100 may be straight.

In an embodiment, the cross section of the cavity 100 a normal of which is parallel to the longitudinal axis of the cavity 100, is round. In an embodiment, the cross section of the cavity 100 may be a circle. In an embodiment, the cavity 100 may have a thread machined to it. The rod 200 of a corresponding cross section may have a similar thread machined to it for making the cavity 100 and the rod 200 to match each other. The cavity 100 with the thread machined to it may be circular and have a constant diameter. The rod 200 may also have a corresponding diameter and a corresponding thread. When the cavity 100 and the rod 200 are threaded, the non-deformed rod 200 may be moved back and forth along the longitudinal axis of the non-deformed cavity 100 by rotating the rod 200 around its longitudinal axis. In other words, the non-deformed rod 200 may be screwed into and from the non-deformed cavity 100. If the rod 200 is deformed or broken, it cannot be rotated which is an indication of the need for maintenance.

In an embodiment, the measuring arm 102 comprising the cavity 100 with or without thread may act as a seat for the attachment of the rod 200 to the cavity 100.

In an embodiment, the cross section of the cavity 100 may be conical. In an embodiment, the cross section of the cavity may be a square, for example. In such an embodiment, the rod 200 may be moved back and/or forth or inserted in the cavity 100 without rotating the rod 200 around its longitudinal axis.

The non-deformed rod 200 has a shape which matches that of the non-deformed cavity 100. In an embodiment, the rod 200 may be insertable to and removable from the non-deformed cavity 100.

In an embodiment, the rod 200 may be located outside of the cavity 100 during the moments or periods when the checking of the need for maintenance is not performed. The cavity 100 and the rod 200 may become permanently mismatched with respect to each other when the measurement arm 102 is permanently bent which causes deformation of the cavity 100. The need for maintenance may then be checked by attempting to insert the rod 200 into the cavity 200. If the rod 200 can be inserted in the cavity 100 with force belonging to a force range used for the non-bent or non-deformed measurement arm 102, the measurement arm 102 is in an acceptable condition and no maintenance is necessary. If the rod 200 cannot be inserted into the cavity 100 or the required force is outside the force range used for the non-bent or non-deformed measurement arm 102, the measurement arm 102 is determined to be in an unacceptable condition and maintenance is necessary.

In an embodiment, the rod 200 may be made of breakable material. The breakable material may be fragile. The breakable rod 200 cannot be bent as much as the measurement arm 102 without breakage. The breakable rod 200 cannot stand sudden impacts without breakage. The breakable material may comprise glass, for example. The breakable material may comprise ceramic material, for example. The breakable material may comprise porcelain, for example. Then the rod 200 may break in the cavity 100 as response to fatigue or an impulse causing bending of the measurement arm 102.

In an embodiment, the rod 200 may be located in the cavity 100 for the cavity 100 and the rod 200 to become mismatched with respect to each other. In this embodiment, the rod 200 may be made of flexible material with irreversibility of a change of shape or of breakable material.

In an embodiment, the rigid and breakable rod 200 may be glued at the bottom 116 of the cavity 100 in order to keep the rod 200 fixed and/or make the rod 200 to tolerate a normal vibration in the consistency measurement.

In an embodiment, the rigid and breakable rod 200 may be glued partly in the cavity 100 in order to keep the rod 200 fixed and/or make the rod 200 to tolerate the normal vibration in the consistency measurement.

In an embodiment, the rigid and breakable rod 200 may be glued over whole length to walls of the cavity 100 in order to keep the rod 200 fixed and/or make the rod 200 to tolerate the normal vibration in the consistency measurement.

However, any impulse stronger than normal to the consistency measurement may break the glued rod 200 made of the breakable material.

Figure 6:
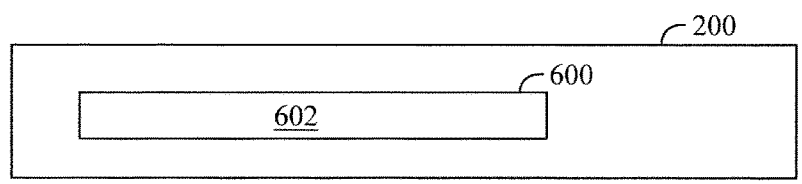
FIG. 6 illustrates an example of a breakable rod having colored liquid in its hollow.

In an embodiment illustrated in FIG. 6, the rod 200 made of breakable material may include a hollow 600 which is filled with liquid 602 of a desired color. In the case the rod 200 is broken, the liquid 602 leaks out from the rod 200. The leakage may, in turn, indicate the need of maintenance.

The liquid 602 may leak into the viscometer 10. The leakage may be noticed or detected and the maintenance be started on the basis of the observation. The viscometer 10 may be periodically continuously monitored for noticing the leakage. For example, if the colored liquid 602 has leaked on the floor or inside the viscometer 10, it is easy to notice. The viscometer 10 may have a transparent window through which it may be seen if the colored liquid 602 has leaked without doing any mechanical work. It may also be possible to monitor and detect the colored liquid 602 with an automatic optical device.

Figure 7:
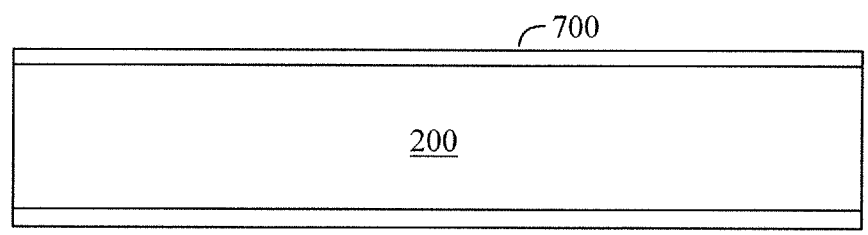
FIG. 7 illustrates of an example of a rod with a metal lining thereover.

In an embodiment an example of which is illustrated in FIG. 7, the breakable rod 200 may at least partly be covered with a metal lining 700 which may have a thread machined to it (in FIG. 7 a full cover is illustrated). The metal lining may be fixed or removable. The metal lining 700 may be a sleeve seal or the like. The lining may make the rod 200 to tolerate the normal vibration in the consistency measurement. However, any impulse stronger than normal may break the rod 200 made of the breakable material.

In an embodiment, the lining 700 with or without thread may act as a seat for the attachment of the rod 200 to the cavity 100.

The difference between a normal vibration and too strong a vibration which doesn't cause a permanent bending of the measurement arm 102 depends on material of the rod 200, thickness of the rod 200 (and/or cavity 100), fixing material (glue) and fabrication tolerances, for example. Although it may be difficult to determine the interface between the two, a breakage of the rod 200 with or without a permanent bending of the measurement arm 102 is always an indication of a need for maintenance.

In an embodiment, the opening 110 of the cavity 100 may be located at a section 112 of the measuring arm 102 which locates outside of a process pipe 114 (see FIGS. 1 to 2 and 4 to 5). This enables the checking of the condition of the measurement arm 102 without a removal of the viscometer 10 from the process pipe 114 and stopping the process. The removal of the viscometer 10 would namely open the process pipe 114 which, in turn, would require the process to be stopped.

It will be obvious to a person skilled in the art that, as technology advances, the inventive concept can be implemented in various ways. The invention and its embodiments are not limited to the example embodiments described above but may vary within the scope of the claims.

The invention claimed is:

1. An apparatus for checking a need for maintenance of a viscometer measuring consistency of suspension, the apparatus comprising:
    a rigid rod and an elongated cavity inside a measuring arm of the viscometer;
    the rigid rod is matched with the cavity for the rod to be movable by rotating around a longitudinal axis in the cavity; and
    the cavity is configured to become mismatched with respect to the rod in response to a bending of the measuring arm, the mismatch indicating a need for maintenance of the viscometer.

2. A viscometer for measuring consistency of suspension, the viscometer comprising:
    a rigid rod and a measuring arm, a first end which is coupled with a projection insertable in the suspension;
    the measuring arm comprises an elongated cavity;
    the rigid rod is matched with the cavity for the rod to be movable by rotating around a longitudinal axis in the cavity; and
    the cavity is configured to become mismatched with respect to the rod in response to a bending of the measuring arm, the mismatch indicating a need for maintenance of the viscometer.

3. The viscometer of claim 2, wherein the cavity is configured to cause at least one of the following to the rod in response to the bending of the measuring arm: immobilization in the cavity, and breakdown of the rod.

4. The viscometer of claim 2, wherein the cross section of the cavity is constant or constantly converging towards the first end, the cavity being configured to deform from a non-deformed configuration to deformed configuration in response to bending of the measuring arm;
    the rod has a shape matching that of the non-deformed configuration, and the rod is insertable to and removable from the non-deformed configuration.

5. The viscometer of claim 2, wherein the rod is made of flexible material a change of shape of which is spontaneously irreversible.

6. The viscometer of claim 2, wherein the rod is located outside of the cavity for the cavity and the rod to become mismatched with respect to each other.

7. The viscometer of claim 2, wherein the rod is made of breakable material.

8. The viscometer of claim 7, wherein the rod is located in the cavity for the cavity and the rod to become mismatched with respect to each other.

9. The viscometer of claim 7, wherein the rod includes a hollow which is filled with liquid of a desired color; and in the case the rod is broken, the liquid leaked out from the rod is configured to indicate the need of maintenance.

10. The viscometer of claim 2, wherein an opening of the cavity being located at a section of the measuring arm located outside of a process pipe.

11. The viscometer of claim 2, wherein the longitudinal axis of the cavity is parallel to that of the measuring arm.

* * * * *